(12) United States Patent
McKinley et al.

(10) Patent No.: US 9,072,861 B2
(45) Date of Patent: Jul. 7, 2015

(54) METHODS AND DEVICES FOR DELIVERING OR DELAYING LIPIDS WITHIN A DUODENUM

(71) Applicant: Endosphere, Inc., Columbus, OH (US)

(72) Inventors: James T. McKinley, Redwood City, CA (US); Zhenyong Keck, Redwood City, CA (US); Fiona M. Sander, Los Altos Hills, CA (US)

(73) Assignee: Endosphere, Inc., Columbus, OH (US)

( * ) Notice: Subject to any disclaimer, the term of this patent is extended or adjusted under 35 U.S.C. 154(b) by 111 days.

(21) Appl. No.: 13/769,097

(22) Filed: Feb. 15, 2013

(65) Prior Publication Data

US 2013/0178782 A1    Jul. 11, 2013

Related U.S. Application Data

(63) Continuation of application No. 12/999,180, filed as application No. PCT/US2009/049586 on Jul. 2, 2009, now abandoned, which is a continuation-in-part of application No. PCT/US2008/070226, filed on Jul. 16, 2008.

(60) Provisional application No. 61/077,579, filed on Jul. 2, 2008.

(51) Int. Cl.
*A61M 27/00*    (2006.01)
*A61F 5/00*    (2006.01)

(52) U.S. Cl.
CPC ............ *A61M 27/002* (2013.01); *A61F 5/0079* (2013.01)

(58) Field of Classification Search
CPC ................ A61F 5/0076; A61F 5/0079; A61F 2250/0023; A61M 27/002
USPC .............. 604/8–9; 623/23.64–23.65; 606/191
See application file for complete search history.

(56) References Cited

U.S. PATENT DOCUMENTS

| | | | |
|---|---|---|---|
| 2,773,502 | A | 12/1956 | Kaslow et al. |
| 3,546,961 | A | 12/1970 | Marton |
| 4,133,315 | A | 1/1979 | Berman et al. |

(Continued)

FOREIGN PATENT DOCUMENTS

| | | |
|---|---|---|
| DE | 4012642 A1 | 10/1991 |
| JP | 01015063 A2 | 1/1989 |

(Continued)

OTHER PUBLICATIONS

Burnett, Daniel R.; U.S. Appl. No. 60/490,421 entitled "Pyloric valve corking device and method," filed Jul. 28, 2003.

(Continued)

*Primary Examiner* — Philip R Wiest
*Assistant Examiner* — Benjamin Klein
(74) *Attorney, Agent, or Firm* — Shay Glenn LLP (57) ABSTRACT

Devices and methods described include a flow reduction device adapted and configured for use within the duodenum of a mammal having a spine, a first atraumatic feature, a second atraumatic feature, and a flow reduction element having a proximal end, a distal end, an interior portion, an exterior portion and a variable porosity between the proximal end and the distal end. One aspect of the device includes a spine having a proximal end and a distal end, an atraumatic feature positioned on at least one of the proximal end and the distal end of the spine, and a flow reduction element positioned along the spine and having a variable porosity along its length.

21 Claims, 4 Drawing Sheets

(56) References Cited

U.S. PATENT DOCUMENTS

| | | |
|---|---|---|
| 4,134,405 A | 1/1979 | Smit |
| 4,315,509 A | 2/1982 | Smit |
| 4,416,267 A | 11/1983 | Garren et al. |
| 4,485,805 A | 12/1984 | Foster, Jr. |
| 4,501,264 A | 2/1985 | Rockey |
| 4,648,383 A | 3/1987 | Angelchik |
| 4,694,827 A | 9/1987 | Weiner et al. |
| 4,878,905 A | 11/1989 | Blass |
| 4,899,747 A | 2/1990 | Garren et al. |
| 5,019,400 A | 5/1991 | Gombotz et al. |
| 5,084,061 A | 1/1992 | Gau et al. |
| 5,234,454 A | 8/1993 | Bangs |
| 5,259,399 A | 11/1993 | Brown |
| 5,329,942 A | 7/1994 | Gunther et al. |
| 5,396,880 A | 3/1995 | Kagan et al. |
| 5,439,476 A | 8/1995 | Frantzides |
| 5,484,610 A | 1/1996 | Bae |
| 5,597,797 A | 1/1997 | Clark |
| 5,820,584 A | 10/1998 | Crabb |
| 5,868,141 A | 2/1999 | Ellias |
| 6,102,922 A | 8/2000 | Jakobsson et al. |
| 6,160,084 A | 12/2000 | Langer et al. |
| 6,187,330 B1 | 2/2001 | Wang et al. |
| 6,264,700 B1 | 7/2001 | Kilcoyne et al. |
| 6,267,988 B1 | 7/2001 | Meyer |
| 6,281,262 B1 | 8/2001 | Shikinami |
| 6,302,917 B1 | 10/2001 | Dua et al. |
| 6,306,163 B1 | 10/2001 | Fitz |
| 6,336,934 B1 | 1/2002 | Gilson et al. |
| 6,365,173 B1 | 4/2002 | Domb et al. |
| 6,388,043 B1 | 5/2002 | Langer et al. |
| 6,402,687 B1 | 6/2002 | Ouchi |
| 6,540,789 B1 | 4/2003 | Silverman et al. |
| 6,579,301 B1 | 6/2003 | Bales et al. |
| 6,635,431 B1 | 10/2003 | Bihain et al. |
| 6,685,957 B1 | 2/2004 | Bezemer et al. |
| 6,716,444 B1 | 4/2004 | Castro et al. |
| 6,720,402 B2 | 4/2004 | Langer et al. |
| 6,740,121 B2 | 5/2004 | Geitz |
| 6,800,056 B2 | 10/2004 | Tartaglia et al. |
| 6,939,557 B2 | 9/2005 | Rowe et al. |
| 6,946,002 B2 | 9/2005 | Geitz |
| 6,953,560 B1 | 10/2005 | Castro et al. |
| 7,025,791 B2 | 4/2006 | Levine et al. |
| 7,037,344 B2 | 5/2006 | Kagan et al. |
| 7,111,627 B2 | 9/2006 | Stack et al. |
| 7,121,283 B2 | 10/2006 | Stack et al. |
| 7,122,058 B2 | 10/2006 | Levine et al. |
| 7,175,669 B2 | 2/2007 | Geitz |
| 7,223,277 B2 | 5/2007 | DeLegge |
| 7,335,210 B2 | 2/2008 | Smit |
| 7,931,693 B2 | 4/2011 | Binmoeller |
| 8,147,561 B2 * | 4/2012 | Binmoeller ............. 623/23.64 |
| 2002/0002384 A1 | 1/2002 | Gilson et al. |
| 2002/0035347 A1 | 3/2002 | Bagaoisan et al. |
| 2002/0035361 A1 | 3/2002 | Houser et al. |
| 2002/0111648 A1 | 8/2002 | Kusleika et al. |
| 2003/0040804 A1 | 2/2003 | Stack et al. |
| 2003/0199990 A1 | 10/2003 | Stack et al. |
| 2004/0015187 A1 | 1/2004 | Lendlein et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0088022 A1 | 5/2004 | Chen |
| 2004/0092892 A1 | 5/2004 | Kagan et al. |
| 2004/0110285 A1 | 6/2004 | Lendlein et al. |
| 2004/0122456 A1 | 6/2004 | Saadat et al. |
| 2004/0153118 A1 | 8/2004 | Clubb et al. |
| 2004/0219186 A1 | 11/2004 | Ayres |
| 2004/0267378 A1 | 12/2004 | Gazi et al. |
| 2005/0004681 A1 | 1/2005 | Stack et al. |
| 2005/0033331 A1 | 2/2005 | Burnett |
| 2005/0033332 A1 | 2/2005 | Burnett et al. |
| 2005/0038415 A1 | 2/2005 | Rohr et al. |
| 2005/0049718 A1 | 3/2005 | Dann et al. |
| 2005/0055014 A1 | 3/2005 | Coppeta et al. |
| 2005/0055039 A1 | 3/2005 | Burnett et al. |
| 2005/0075405 A1 | 4/2005 | Wilson et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0090873 A1 | 4/2005 | Imran |
| 2005/0119674 A1 | 6/2005 | Gingras |
| 2005/0125020 A1 | 6/2005 | Meade et al. |
| 2005/0125075 A1 | 6/2005 | Meade et al. |
| 2005/0183732 A1 | 8/2005 | Edwards |
| 2005/0238694 A1 | 10/2005 | Gerhardt et al. |
| 2005/0245719 A1 | 11/2005 | Mather et al. |
| 2005/0273060 A1 | 12/2005 | Levy et al. |
| 2005/0277975 A1 | 12/2005 | Saadat et al. |
| 2006/0020278 A1 | 1/2006 | Burnett et al. |
| 2006/0064120 A1 | 3/2006 | Levine et al. |
| 2006/0079944 A1 | 4/2006 | Imran |
| 2006/0086362 A1 | 4/2006 | Solomon |
| 2006/0129237 A1 | 6/2006 | Imran |
| 2006/0142794 A1 | 6/2006 | Lendlein et al. |
| 2006/0155311 A1 | 7/2006 | Hashiba et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0247718 A1 | 11/2006 | Starkebaum |
| 2006/0259051 A1 | 11/2006 | Nissl |
| 2006/0265082 A1 | 11/2006 | Meade et al. |
| 2006/0282107 A1 | 12/2006 | Hashiba et al. |
| 2007/0005147 A1 | 1/2007 | Levine et al. |
| 2007/0010864 A1 | 1/2007 | Dann et al. |
| 2007/0010865 A1 | 1/2007 | Dann et al. |
| 2007/0027548 A1 | 2/2007 | Levine et al. |
| 2007/0083271 A1 | 4/2007 | Levine et al. |
| 2007/0110793 A1 | 5/2007 | Kantrowitz et al. |
| 2007/0135768 A1 | 6/2007 | Carlsen |
| 2007/0156159 A1 * | 7/2007 | Gannoe et al. ............. 606/153 |
| 2007/0156248 A1 | 7/2007 | Marco et al. |
| 2007/0239284 A1 | 10/2007 | Skerven et al. |
| 2007/0265598 A1 | 11/2007 | Karasik |
| 2007/0282418 A1 | 12/2007 | Weitzner |
| 2007/0293885 A1 | 12/2007 | Binmoeller et al. |
| 2008/0065136 A1 | 3/2008 | Young |
| 2008/0097510 A1 | 4/2008 | Albrecht et al. |
| 2008/0234834 A1 | 9/2008 | Meade et al. |
| 2009/0187206 A1 | 7/2009 | Binmoeller et al. |
| 2011/0137227 A1 | 6/2011 | McKinley et al. |
| 2011/0190684 A1 | 8/2011 | Binmoeller |
| 2012/0172999 A1 | 7/2012 | Binmoeller |
| 2013/0109912 A1 | 5/2013 | Binmoeller et al. |
| 2014/0100513 A1 | 4/2014 | Binmoeller |
| 2014/0114228 A1 | 4/2014 | Binmoeller et al. |

FOREIGN PATENT DOCUMENTS

| | | |
|---|---|---|
| JP | 2004509714 | 4/2004 |
| WO | WO 89/00407 A1 | 1/1989 |
| WO | WO 03/094785 A1 | 11/2003 |
| WO | WO 2004/041133 A1 | 5/2004 |
| WO | WO 2004/093753 A2 | 11/2004 |
| WO | WO 2005/120363 A1 | 12/2005 |
| WO | WO 2006/044640 A1 | 4/2006 |
| WO | WO 2006/092789 A2 | 9/2006 |
| WO | WO 2006/102240 A2 | 9/2006 |
| WO | WO 2007/030829 A2 | 3/2007 |
| WO | WO 2007/053556 A1 | 5/2007 |
| WO | WO 2007/053706 A1 | 5/2007 |
| WO | WO 2007/053707 A1 | 5/2007 |
| WO | WO 2007/075396 A2 | 7/2007 |
| WO | WO 2007/139920 A2 | 12/2007 |
| WO | WO 2008/001381 A2 | 1/2008 |
| WO | WO 2009/012335 A1 | 1/2009 |

OTHER PUBLICATIONS

Burnett, Daniel R.; U.S. Appl. No. 60/525,105 entitled "Intragastric therapeutic device and method," filed Nov. 28, 2003.

(56) References Cited

OTHER PUBLICATIONS

Asakawa et al., "Characterization of the effects of pancreatic polypeptide in the regulation of energy balance," Gastroenterology 124(5):1325-36 (May 2003).
Batterham et al., "Gut hormone PYY(3-36) physiologically inhibits food intake," Nature 418(6898): 650-4 (Aug. 8, 2002).
Batterham et al., "Inhibition of food intake in obese subjects by peptide YY3-36," 0N Engl J Med., 349(10):941-8 (Sep. 4, 2003).
Batterham et al., "Pancreatic polypeptide reduces appetite and food intake in humans," J Clin Endocrinol Metab. 88(8):3989-92 (Aug. 2003).
Caro et al., "Leptin: the tale of an obesity gene," Diabetes 45(11): 1455-62 (Nov. 1996).
Chapman et al., "Effects of small-intestinal fat and carbohydrate infusions on appetite and food intake in obese and nonobese men," Am J Clin Nutr, vol. 69, pp. 6-12 (Jan. 1999).
Cohen et al., "Oxyntomodulin suppresses appetite and reduces food intake in humans," J Clin Endocrinol Metab., 88(10): 4696-4701 (Oct. 2003).
Collins et al., "Role of leptin in fat regulation," Nature, 380 (6576):677 (Apr. 25, 1996).
D'Alessio et al., "Activation of the parasympathetic nervous system is necessary for normal meal-induced insulin secretion in rhesus macaques," J Clin Endocrinol Metab., 86(3): 1253-9 (Mar. 2001).
Davis et al., "Distension of the small intestine, satiety, and the control of food intake," Am Journal of Clinical Nutrition, vol. 31, pp. S255-S258 (Oct. 1978).
de Castro et al., "A general model of intake regulation," Neuroscience and Biobehavioral Reviews, vol. 26(5), pp. 581-595 (Aug. 2002).
French et al.,"Is Cholecystokinin a Satiety Hormone? Correlations of Plasma Cholecystokinin with Hunger, Satiety, and Gastric Empyting in Normal Volunteers," Appetite, vol. 16, pp. 95-104 (Oct. 1993).
Gao et al., "Sensory and biomechanical responses to ramp-controlled distension of the human duodenum," Am. J. Physiol. Gas., vol. 284, pp. G461-G471 (Mar. 2003).
Geliebter et al., "Clinical trial of silicone rubber gastric balloon to treat obesity," Int J Obesity, 15(4): 259-266 (Apr. 1991).
Ghatei et al., Molecular forms of human enteroglucagon in tissue and plasma: plasma responses to nutrient stimuli in health and in disorders of the upper gastrointestinal tract, J Clin Endocrinol Metab, 57(3):488-95 (Sep. 1983).
Gibbs et al., "Cholecystokinin descreases food intake in rats," J Comp Physiol Psychol. 84(3):488-95 (Sep. 1973).
Havel, Peter, "Peripheral signals conveying metabolic information to the brain: Short-term and long-term regulation of food intake and energy homeostasis," Society for Experimental Biology and Medicine, vol. 226, pp. 963-977 (Dec 2001).
Havel, PJ, "Role of adipose tissue in body-weight regulation: mechanisms regulating leptin production and energy balance," Proc Nutr Soc. 59(3):359-71 (Aug. 2000).
Haynes et al., "Receptor-mediated regional sympathetic nerve activation by leptin," J Clin Invest. 100(2): 270-278 (Jul. 15, 1997).
Herrmann et al., "Glucagon-like peptide-1 and glucose-dependent insulin-releasing polypeptide plasma levels in response to nutrients," Digestion 56(2);117-26; (year of publication is sufficiently earlier than the effective U.S. filing and any foreign priority date ) 1995.
Kissileff et al., "Peptides that Regulate Food Intake: Cholecystokinin and stomach distension combine to reduce food intake in humans," Am J Physiol Regul Integr Comp Physiol., 285(5):R992-8 (Nov. 2003).
Le Quellec et al., "Oxyntomodulin-like immunoreactivity: diurnal profile of a new potential entergastrone," J Clin Endocrinol Metab, 74(6): 1405-9 (Jun. 1992).
Levin et al., "Decreased food intake does not completely account for adiposity reduction after ob protein infusion," Proc Natl Acad Sci U.S.A., 93(4): 1726-30 (Feb. 20, 1996).

Liddle et al., "Cholecystokinin bioactivity in human plasma. Molecular forms, responses to feeding, and relationship to gallbladder contraction," J Clin Invest. 75(4):1144-52 (Apr. 1985).
Lindor et al., "Intragastric balloons in comparison with standard therapy for obesity—a randomized, double-blind trial," Mayo Clin Proc 62(11): 992-6 (Nov. 1987).
Malaisse-Lagae et al., "Pancreatic polypeptide: a possible role in the regulation of food intake in the mouse. (Hypothesis)" Experientia 15; 33(7):915-917 (Jul. 15, 1977).
Mathus-Vliegen et al., "Intragastric balloon in the treatment of super-morbid obesity. Double-blind, sham-controlled, crossover evaluation of 500-millimeter balloon," Gastroenterology, 99(2): 362-369 (Aug. 1990).
Moran el al, "Neurobiology of cholecystokinin," Crit Rev Neurobiol. 9(1): 1-28 (year of publication is sufficiently earlier than the effective U.S. filing and any foreign priority date) 1994.
Moran et al., "Gastrointestinal satiety signals," Am J Physiol Gastrointest Liver Physiol, vol. 286, pp. G183-G188 (Feb. 1, 2004).
Näslund et al., "GLP-1 slows solid gastric emptying and inhibits insulin, glucagon, and PYY release in humans," Am J Physiol 277 (3 Pt 2):R910-R916 (Sep. 1999).
Rayner et al., "Effects of cholecystokinin on appetite and pyloric motility during physiological hyperglycermia," Am J. Physiol. Gastrointest. Liver Physiol. , vol. 278, pp. G98-G104 (Jan. 2000).
Read et al., "The Role of the Gut in Regulating Food Intake in Man," Nutrition Reviews, vol. 52, pp. 1-10 (Jan. 1994).
Read, N.W. "Role of gastrointestinal factors in hunger and satiety in man," Proceedings of the Nutrition Society, vol. 51, pp. 7-11 (May 1992).
Remington: The Science and Practice of Pharmacy, 20th Ed., Chap. 47, Controlled Release Drug Delivery Systems. (Jun. 2003).
Remington's Pharmaceutical Sciences, 17th Ed.; A. R. Gennaro (Editor); "Freeze-drying," p. 1538-1539 (year of publication is sufficiently earlier than the effective U.S. filing and any foreign priority date) 1985.
Rigaud et al., "Gastric distension, hunger, and energy intake after balloon implantation in severe obesity," Int J Obes Relat Metab Disor., 19(7):489-95 (Jul. 1995).
Ritter, Robert C.; Gastrointestinal mechanisms of satiation for food; Physiol Behav.; 81(2):249-73; Apr. 2004.
Scarpace et al., "Leptin increases uncoupling protein expression and energy expenditure," Am J Physiol., 273 (1 Pt 1): E226-230 (Jul. 1997).
Schirra et al., Mechanisms of the antidiabetic action of subcutaneous glucagon-like peptide-1 (7-36)amide in non-insulin dependent diabetes mellitus, J Endocrinol. 156(1):177-86 (Jan. 1998).
Schwartz et al., "Central nervous system control of food intake," Nature, 404(6778): 661-671 (Apr. 6, 2000).
Schwartz et al., "Keeping hunger at bay," Nature, vol. 418, pp. 595-597; Aug. 8, 2002.
Schwartz et al., "Model for the regulation of energy balance and adiposity by the central nervous system," Am J Clin Nutr., 69(4): 584-96 (Apr. 1999).
Standring, Susan (ed). Gray's Anatomy, 39th Ed. 1163-64; Nov. 24, 2004.
Wang et al.; Upper intestinal lipids trigger a gut-brain-liver axis to regulate glucose production; Nature; vol. 452; pp. 1012-1016 (Apr. 24, 2008).
Wilding, J. P. H., "Neuropeptides and appetite control," Diabetes U.K. Diabetic Medicine, vol. 19, pp. 619-627 (Aug. 2002).
Woods et al., "The Regulation of Food Intake by Peptides," Annals of the New York Academy of Sciences, vol. 575. pp. 236-243; Dec. 1989.
Wynne et al., "Appetite control," Journal of Endocrinology, vol. 184, pp. 291-318; Feb. 2005.
Binmoeller, K.; U.S. Appl. No. 13/768,659 entitled "Methods and devices to curb appetite and/or reduce food intake," filed Feb. 15, 2013.

* cited by examiner

METHODS AND DEVICES FOR DELIVERING OR DELAYING LIPIDS WITHIN A DUODENUM

CROSS REFERENCE TO RELATED APPLICATIONS

This application is a continuation of U.S. patent application Ser. No. 12/999,180, filed Jan. 31, 2011, entitled "METHODS AND DEVICES FOR DELIVERING OR DELAYING LIPIDS WITHIN A DUODENUM," now Publication No. 2011-0137227, which is a 35 U.S.C. §371 national phase application of International Patent Application No. PCT/US2009/049586, filed Jul. 2, 2009, entitled "METHODS AND DEVICES FOR DELIVERING OR DELAYING LIPIDS WITHIN A DUODENUM," now Publication No. WO 2010/003097, which claims the benefit of priority of U.S. Provisional Patent Application No. 61/077,579, filed Jul. 2, 2008, entitled "METHODS AND DEVICES FOR DELIVERING OR DELAYING LIPIDS WITHIN A DUODENUM" and is also a continuation-in-part of International Patent Application No. PCT/US2008/070226, filed Jul. 16, 2008, entitled "CONFORMATIONALLY-STABILIZED INTRALUMINAL DEVICE FOR MEDICAL APPLICATIONS," now Publication No. WO 2009/012335 A1, the entirety of each of these applications is incorporated herein by reference in its entirety.

Various aspects of the design, function, deployment, operation and delivery of conformal flow reduction devices for use in the duodenum are described in the following related applications: U.S. Provisional Patent Application No. 60/950,071, filed Jul. 16, 2007, entitled "CONFORMATIONALLY-STABILIZED INTRALUMINAL DEVICE FOR MEDICAL APPLICATIONS," now International Patent Application No. PCT/US2008/070226, filed Jul. 16, 2008, entitled "A CONFORMATIONALLY-STABILIZED INTRALUMINAL DEVICE FOR MEDICAL APPLICATIONS," now Publication No. WO 2009/012335; U.S. patent application Ser. No. 10/999,410, filed Nov. 30, 2004, entitled "METHOD AND APPARATUS FOR REDUCING OBESITY," now U.S. Pat. No. 7,931,693; U.S. patent application Ser. No. 11/300,283, filed Dec. 15, 2005, entitled "METHODS AND DEVICES TO CURB APPETITE AND/OR REDUCE FOOD INTAKE," now U.S. Pat. No. 8,147,561; and U.S. patent application Ser. No. 11/807,107, filed May 25, 2007, entitled "METHODS AND DEVICES TO CURB APPETITE AND/OR REDUCE FOOD INTAKE," now Publication No. 2007-0293885.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Obesity and type 2 diabetes are diseases of insufficient or deficient regulation. We know from human studies that the small intestine plays a critical role in both energy and glucose homeostasis: when the duodenum is exposed to lipids, appetite is diminished and native (liver) glucose production is down-regulated. Previously we have invented a device that can be implanted into the duodenum and remain in place; we have described devices and methods for slowing the passage of food through the duodenum to cause increased tissue-nutrient contact, thereby causing amplified hormonal signaling from the duodenum; and, we have invented methods and devices for delivering chemicals, drugs or other compounds to the duodenum.

What is needed are devices and/or methods for additional lipid uptake, delaying ingesta passage/prolonging ingesta contact, delivering or providing lipids or other appetite and glucose reducing nutrients and/or combinations of these characteristics.

SUMMARY OF THE DISCLOSURE

In one aspect of the present invention, there is provided a device adapted and configured for use within the duodenum of a mammal. The device has a spine having a proximal end and a distal end; an atraumatic feature positioned on at least one of the proximal end and the distal end of the spine; and, positioned along the spine, a flow reduction element having variable porosity along its length. In one embodiment, the variable porosity of the flow reduction element is selected so that a portion of a flow over the proximal end of the flow reduction element flows into an interior portion of the flow reduction element. In one embodiment, the variable porosity of the flow reduction element is selected so that flow within an interior of the flow reduction element is at least partially inhibited from flowing through the distal portion of the variable porosity structure. In one embodiment, the proximal portion of the flow reduction element comprises a material, a mesh or a braid having a porosity or altered to provide a porosity selected to permit a flow into an interior portion of the flow reduction element. In one embodiment, the distal portion of the flow reduction element comprises a material, a mesh or a braid having a porosity or altered to provide a porosity selected to at least partially inhibit a flow from within an interior portion of the flow reduction element. In one embodiment, the length of the spine is selected so when the atraumatic feature is positioned in a stomach the flow reduction element is positioned on the spine and distal to a pylorus. In one embodiment, the length of the spine is selected so when the atraumatic feature is positioned in a stomach the distal end of the spine is in the fourth portion of the duodenum and the flow reduction element is positioned within a portion of the duodenum. In one embodiment, there is also a flow reduction element having a non-variable porosity along its length. In one embodiment, there is also a feature on the spine positioned to restrict movement of the flow reduction element relative to the spine.

In still another aspect of the present invention, there is provided a device adapted and configured for use within the duodenum of a mammal. The device has a spine with a length, a proximal end and a distal end; a first atraumatic feature positioned adjacent to the spine proximal end; a second atraumatic feature positioned adjacent to the spine distal end wherein the length of the spine is selected so that when the first atraumatic feature is in the stomach the second atraumatic feature is in the fourth portion of the duodenum; and a flow reduction element having a proximal end, a distal end, an interior portion, an exterior portion and a variable porosity between the proximal end and the distal end. In one embodiment, the porosity of the proximal end is selected to the allow flow to pass from the exterior portion to the interior portion. In one embodiment, the porosity of the distal end is selected to impede flow from the interior portion to the exterior portion. In one embodiment, the proximal portion is more porous than the distal portion. In one embodiment, the proximal end has a porous structure configured to permit flow into the interior portion and the distal end has a solid portion to retain material within the interior portion. In one embodiment, there is provided another flow reduction element between the proximal and distal ends of the spine. In one embodiment, the another flow reduction element has variable porosity between the proximal and distal ends of the flow reduction element. In one embodiment, the length of the spine is selected so that when the first atraumatic feature is positioned in a stomach the second atraumatic feature is positioned within the duodenum and adjacent to the first atraumatic feature. In one embodiment, the length of the spine is selected so that when the first atraumatic feature is positioned in a stomach the second atraumatic feature is positioned within the duodenum and in proximity to the ligament of Treitz.

In still another aspect, there is provided a method for adjusting the passage of ingesta through the duodenum of a mammal by placing the distal end of a flow reduction device in the duodenum of a mammal; placing the proximal end of the flow reduction device in a stomach of the mammal; expanding within the duodenum of the mammal a variable porosity flow reduction element supported by the flow reduction device; and directing at least a portion of the flow of ingesta through the duodenum through the proximal end of the variable porosity flow reduction element and into an interior portion of the variable porosity flow reduction element. In one embodiment, there is also provided a method retaining a portion of the ingesta within the interior portion of the variable porosity flow reduction element until the ingesta is pushed out of the interior portion by peristaltic action of the duodenum. In still another embodiment, there is provided a method of adjusting the passage of ingesta wherein the ingesta is pushed out of the interior portion by passing through a distal portion of the variable porosity flow reduction element. In still another alternative method for adjusting the passage of ingesta, the ingesta is pushed out of the interior portion by passing through the proximal portion and thereafter passing around the variable porosity flow reduction element.

In another aspect, the flow reduction elements positioned along the device backbone could be coated with, manufactured from or contain lipid-philic materials. For example, one or more of the flow reduction elements of the intraduodenal device could be manufactured from a lipid absorbing or adsorbing material. A flow reduction element manufactured in this way will attract and collect lipids from passing ingesta and hold the lipids for a period of time. The length of time that the lipids will remain attached to the flow reduction element will vary based on a number of factors. For example, the flow reduction element may exude the lipids as peristalsis continues to squeeze the device. The prolonged presence of and/or sustained release of lipids within the duodenum is believed to benefit and in some cases to increase hormonal regulation. It is to be appreciated that embodiments of the present invention provide prolonged presence of and/or sustained release of lipids within the duodenum through the use of one or more of: making flow reduction elements and/or other components of the flow reduction device (i.e., any of the components of FIG. 1 for example) at least partially or even completely from one or more lipid-philic materials; coating flow reduction elements and/or other components of the flow reduction device entirely or at least partially form lipid-philic materials; and/or placing within a flow reduction element, or attaching to a component of the flow reduction device an additional element or component formed from or at least partially coated with a lipid-philic material.

DETAILED DESCRIPTION

The present application relates to methods and devices for providing a sense of fullness/satiety and/or glucose production inhibition. The devices and methods described herein provide for additional lipid presence in the duodenum by delaying ingesta passage/prolonging ingesta contact, delivering or providing lipids or other satiety and/or glucose reducing nutrients and/or combinations thereof.

Lipids can be generally defined as substances such as a fat, oil or wax that dissolve in alcohol but not in water. Lipids contain carbon, hydrogen and oxygen but have far less oxygen proportionally than carbohydrates. They serve as a source of fuel and are an important constituent of the structure of cells. As used herein, lipids refer to any of fatty acids, glycerides, complex lipids and nonglycerides. Fatty acids include both saturated and unsaturated. Glycerides include, for example, neutral phosphoglycerides. Complex lipids are lipids complexed with another type of chemical compound and include, for example, lipoproteins, phospholipids and glycolipids. Nonglycerides include, for example, sphingolipds, steroids and waxes.

Because most ingesta contain lipids, it is believed that the methods and devices described herein for prolonging lipid residence time, delaying lipid passage and/or providing lipids would enhance the operating characteristics of a duodenal positioned flow reduction device, such as those described in the related applications. In other words, the methods and devices described herein not only slow the passage of food but may also detain or delay the passage of food. The delay or detention may allow for prolonged nutrient release and aid in achieving health objectives. Additionally or alternatively, the devices and methods described herein may also provide for active introduction of lipids into the duodenum.

Catch and hold food, some of which is lipid. By using flow reduction bulges along the spine of the device pictured in FIG. 1, ingesta can be caught and held temporarily. The mesh bulges may have a more open structure on the end from which nutrients arrive from the stomach and smaller openings on the end from which nutrients depart as one way to hold nutrients longer. Alternatively, the spheres could themselves become 'buckets' in which food is captured and retained. The bucket may be provided by having a solid bottom portion so that chyme entering remains in the bottom of the bucket until pushed out by peristaltic action or my movement of additional chyme to displace it.

The flow restriction devices may be any of a wide variety of shapes and dimensions as described in the incorporated patent applications. The adjustment of the flow characteristics of ingesta or chyme: (a) around the outside of a flow reduction element, (b) through a wall of a flow or portion of a flow reduction element and (c) retained within a flow reduction element may be accomplished in a number of ways. One way to adjust the flow characteristics within a flow regulated duodenum (i.e., a duodenum having a flow reduction device implanted within it) is through the porosity or flow characteristics of the flow reduction elements.

Figure 1:
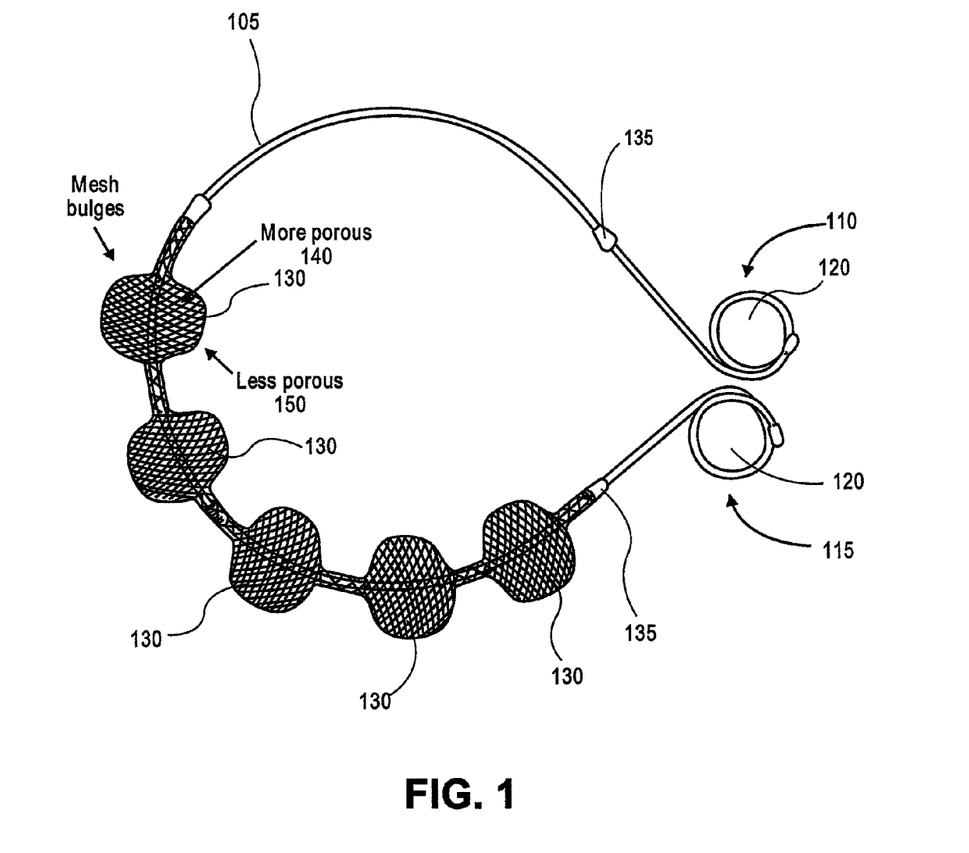
FIG. 1 is a prospective view of a device for use in the duodenum.

FIG. 1 illustrates a perspective view of a device 100 having a spine 105, a proximal end 110, a distal end 115, atraumatic features 120 on both the proximal and distal ends. A series of five flow reduction elements 130 are shown in position along the spine 105. There may be one or more features 135 on the spine to prevent unwanted proximal or distal movement of the flow reduction elements 130 along the spine 105. The flow reduction elements 130 are shown in a deployed configuration as they would be in use within the duodenum. In the most basic form, one or more of the flow reduction elements may be formed from a material or materials with porosity characteristics that adjust the flow characteristics of chyme or ingesta flow relative to the material and the flow reduction element.

As shown in FIG. 1, the device 100 is orientated as it would be implanted with the proximal end 110 in the stomach and the distal end 115 in the duodenum near the ligament of Trietz. Chyme/ingesta flow is from the proximal end 110 to the distal end 115 in FIG. 1. The more porous portion of the flow reduction element 140 will interact with the chyme first. Because of the porosity of this part of the flow reduction element, chyme will flow into the interior portion of the flow reduction element as well as around the flow reduction element. As peristaltic action in the duodenum continues to move the chyme, the portion inside of the flow reduction element is urged distally towards the portion of the flow reduction device that is less porous 150. Some of the chyme entering the flow reduction element portion 150 will be retained within the flow reduction element for some period of time based upon a number of factors such as how much the person has eaten and the porosity of this portion of the flow reduction element among others. As a result of the variable porosity of the structure of the flow reduction element, chyme enters but then is delayed in leaving the flow reduction element interior. It is believed that increasing the residence time of chyme within a flow reduction element will increase the time of interaction of the nutrients in that trapped portion and/or provide for an extended release of the lipids in the trapped portion of chyme. The retained food could be nutrient rich or lipid rich so that the prolonged exposure produces a sense of satiety and/or the inhibition of liver glucose production in the individual. One such mechanism that may be achieved or fostered by the embodiments described herein is described in "Upper intestinal lipids trigger a gut-brain-liver axis to regulate glucose production" by Penny Y. T. Wang et al (Nature, Vol. 452:24 April 2008 doi:10.1038/nature06852).

Figure 2:
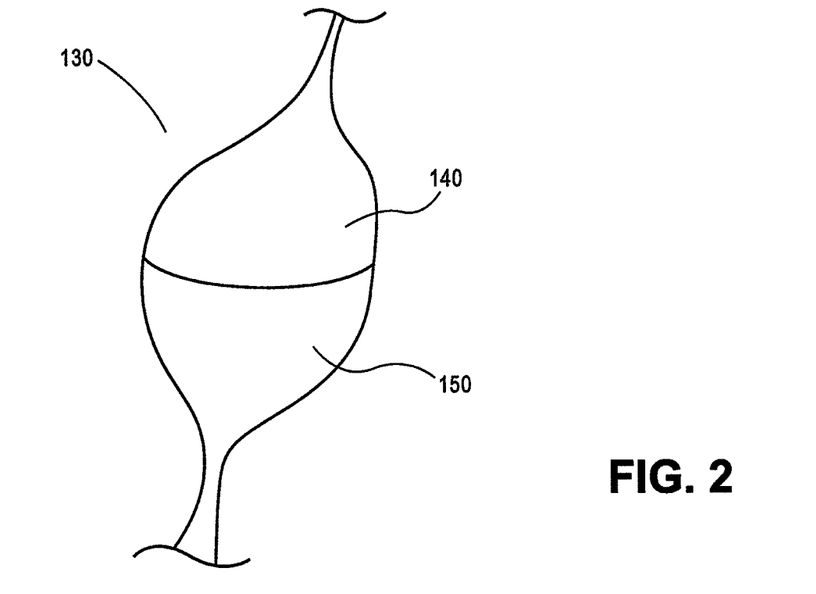
FIG. 2 is an enlarged view of one of the flow reduction elements of FIG. 1 showing the upper and lower portions of the element.
Figure 2A:
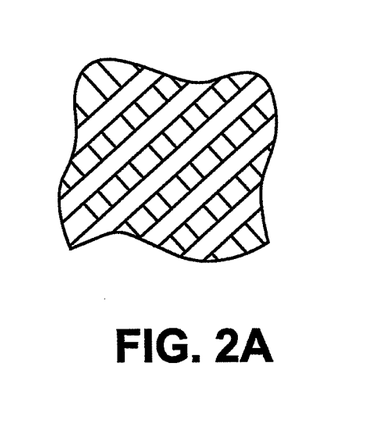
FIG. 2A is an enlarged view of a material used to provide variable porosity to a flow portion of a flow reduction element.
Figure 2B:
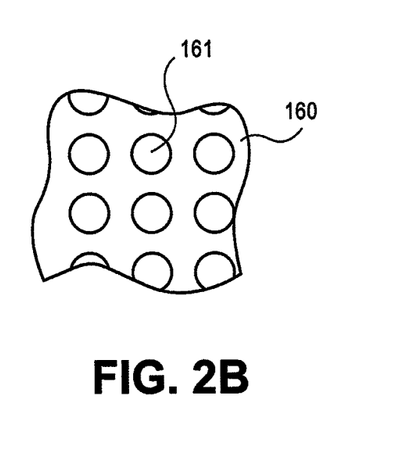
FIG. 2B is an enlarged view of a solid or semi permeable sheet where a pattern of holes are used to provided variable porosity to a portion of a flow reduction element.

The flow characteristics of the flow reduction element may be adjusted in a number of ways. FIG. 2 is an enlarged view of a flow reduction element 130 in FIG. 1. The flow reduction element is divided roughly in half with an upper portion 140 (the part to first contact with the flow of chyme) having a porosity that allows flow through it and into the interior of the flow reduction element. The bottom portion 150 of the flow reduction element is less porous or allows less flow of chyme from the interior of the flow reduction element. The variable porosity or flow characteristics of the flow reduction elements may be adjusted by selecting material with different sizes (FIG. 2A), shapes, construction, and/or filaments with different characteristics to enhance or diminish flow as needed for the upper or lower portions. The flow characteristics of a flow reduction element may be obtained by overlapping (i.e., joined or crossed without joining) filaments to form cells that will, to the desired degree, permit or impede chyme passage. Alternatively or additionally, the flow reduction element could be formed from a solid or semi-permeable sheet 160 with holes 161 formed in it as shown in FIG. 2B. The size, shape, pattern and distribution of the openings may be used to adjust the amount of relative flow through a flow reduction element.

Figure 3:
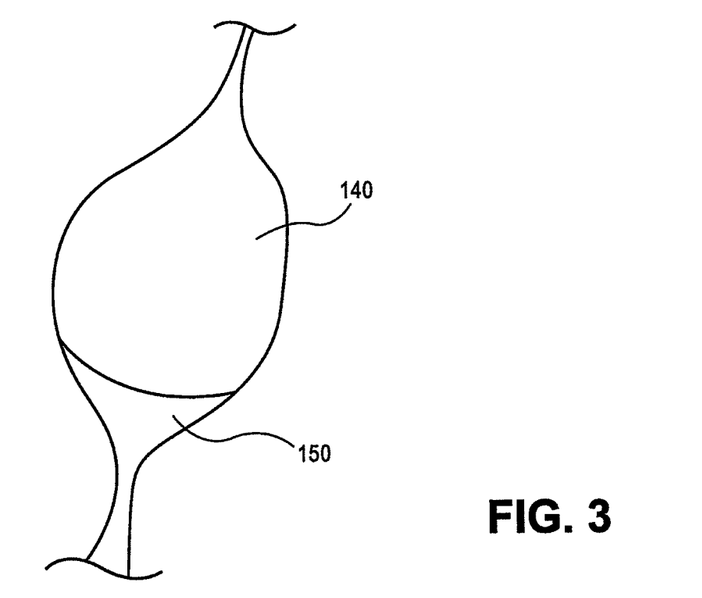
FIG. 3 illustrates a flow reduction element embodiment where more of the flow reduction device is utilized for allowing flow through the use of a larger proximal portion having a more porous construction and a smaller distal portion having a less porous construction.
Figure 4:
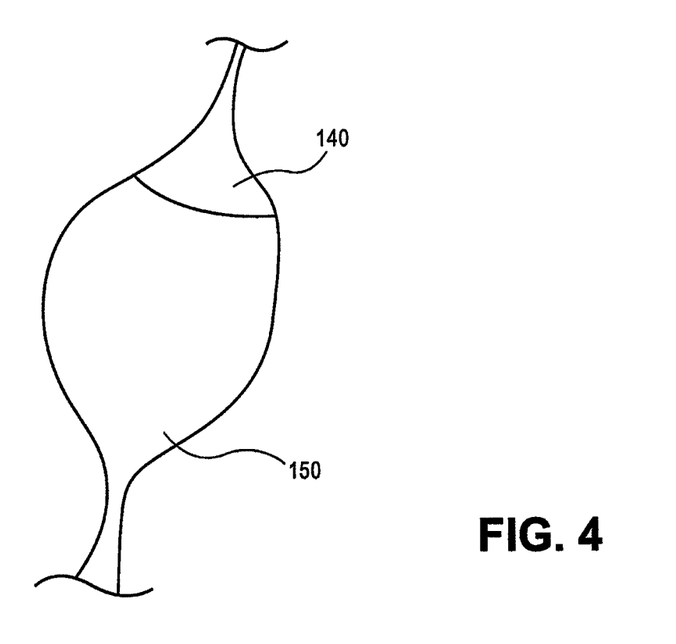
FIG. 4 illustrates a flow reduction element embodiment where more of the flow reduction device is utilized for preventing flow than for allowing flow through the use of a smaller proximal portion having a more porous construction and a larger distal portion having a less porous construction.

The flow reduction element adjustment may also be accomplished by adjusting the relative amounts of the flow reduction element used for allowing flow (more porous 140) or preventing flow (less porous 150). FIG. 3 illustrates a flow reduction element embodiment where more of the flow reduction device is utilized for allowing flow than for preventing flow. In contrast, FIG. 4 illustrates a flow reduction element embodiment where more of the flow reduction device is utilized for preventing flow than for allowing flow.

The foregoing are merely examples. More than one flow allowing or more than one flow preventing zone or portion may be used in a flow reduction element. While the relative distribution of the flow zones has been generally perpendicular to the spine or flow within the duodenum, other orientations relative to the spine or the duodenum are possible depending upon the desired flow profile. Moreover, a device may have flow reduction elements having one or more flow adjustment zones, or no flow adjustment zones. The type of flow reduction elements and the flow characteristics of those flow reduction elements may be mixed within a flow reduction device depending upon the desired flow characteristics desired.

Other flow reduction element properties such as the shape and size of a reduction element, the relative size between reduction elements, the alignment or orientation of a reduction element to the central shaft or spine and other properties are further described in the incorporated applications and may also be adjusted to accomplish the nutrient delivery aspects described herein.

Alternatively, the flow reduction elements could also be configured to capture and hold a lipid For instance, to maintain a certain lipid level in the spheres, the patient could periodically swallow a lipid 'pill' or other form that engages the device and remains in place. The nutrient could also take the form of an extended release compound that releases an amount of the nutrient over time. The nutrient could also be mixed with another compound that is released when the patient consumes a releasing agent, such as before a meal or at a time of day prone to hunger pangs or higher than desired blood glucose levels. The releasing agent mixes with the nutrient compound mixture causing the release of nutrients, such as lipids, to aid in regulation of hunger and/or glucose.

In another aspect, the flow reduction device could be coated with, manufactured with or contain nutrients such as lipids or lipid-philic materials. For example, the flow reduction elements could be one or more bulges manufactured using lipid leaching materials; or the bulges could be manufactured with lipid-philic materials or a sponge like membrane inside the bulges or otherwise connected to the device backbone, that would absorb and distribute temporally lipids from passing ingesta to increase hormonal regulation.

In another aspect, the flow reduction elements positioned along the device backbone could be coated with, manufactured from or contain lipid-philic materials. For example, one or more of the flow reduction elements of the intraduodenal device could be manufactured from a lipid absorbing or adsorbing material. A flow reduction element manufactured in this way will attract and collect lipids from passing ingesta and hold the lipids for a period of time. The length of time that the lipids will remain attached to the flow reduction element will vary based on a number of factors. For example, the flow reduction element may exude the lipids as peristalsis continues to squeeze the device. The prolonged presence of and/or sustained release of lipids within the duodenum is believed to benefit and in some cases to increase hormonal regulation. It is to be appreciated that embodiments of the present invention provide prolonged presence of and/or sustained release of lipids within the duodenum through the use of one or more of: making flow reduction elements and/or other components of the flow reduction device (i.e., any of the components of FIG. 1 for example) at least partially or even completely from one or more lipid-philic materials; coating flow reduction elements and/or other components of the flow reduction device entirely or at least partially form lipid-philic materials; and/or placing within a flow reduction element, or attaching to a component of the flow reduction device an additional element or component formed from or at least partially coated with a lipid-philic material., The spine could be configured as a central tube with plural inlet/outlet ports in communication with a flow reduction element and/or the outside of the tube as described in the incorporated applications. Additionally or alternatively, a portion of the device itself, i.e.: the backbone or spine, could be hollow such that it could be filled with lipids that would leach out or otherwise be delivered to the duodenum. A nutrient reservoir may be implanted within the patient, within the flow reduction device or separately injected into the device during implantation, after insertion or periodically while the patient has the device inserted in his duodenum.

Additionally or alternatively, the lipid equipped hormonal regulatory device could be configured to release lipids on demand using an internal or external controller or device as described in U.S. patent application Ser. No. 11/807,107, filed May 25, 2007, entitled "METHODS AND DEVICES TO CURB APPETITE AND/OR REDUCE FOOD INTAKE," now Publication No. 2007-0293885.

What is claimed is:

1. A device adapted and configured for use within the duodenum of a mammal, comprising:
   a spine having a proximal end and a distal end;
   an atraumatic feature positioned on at least one of the proximal end and the distal end of the spine; and
   a flow reduction element positioned along the spine, the flow reduction element having a proximal portion with a first porosity and a distal portion with a second porosity, the first porosity greater than the second porosity such that the proximal portion permits a flow of chyme into an interior of the flow reduction element while the distal portion at least partially inhibits the flow of chyme out of the interior of the flow reduction element.

2. The device of claim 1 wherein the proximal portion of the flow reduction element comprises a material, a mesh or a braid having a porosity or altered to provide a porosity selected to permit the flow of chyme into the interior of the flow reduction element.

3. The device of claim 1 wherein the distal portion of the flow reduction element comprises a material, a mesh or a braid having a porosity or altered to provide a porosity selected to at least partially inhibit the flow of chyme from within the interior of the flow reduction element.

4. The device of claim 1 wherein the flow reduction element is positioned along the spine so when the atraumatic feature is positioned in a stomach the flow reduction element is positioned distal to a pylorus.

5. The device of claim 1 wherein a length of the spine is selected so when the atraumatic feature is positioned in a stomach the distal end of the spine is in the fourth portion of the duodenum and the flow reduction element is positioned within a portion of the duodenum.

6. The device of claim 1, wherein the flow reduction element is at least partially formed from a lipid-philic material.

7. The device of claim 1 wherein at least a portion of the interior of the flow reduction element is at least partially coated with a lipid-philic material.

8. The device of claim 1 wherein the flow reduction element is configured to deform in shape in response to a peristaltic action of the duodenum.

9. The device of claim 1 wherein at least a portion of an exterior of the flow reduction element is at least partially coated with a lipid-philic material.

10. The device of claim 1 further comprising:
    a lipid-philic structure within the flow reduction element.

11. The device of claim 10 wherein the lipid-philic structure within the flow reduction element is attached to the spine.

12. The device of claim 10 wherein the lipid-philic structure within the flow reduction element is attached to the flow reduction element.

13. A device adapted and configured for use within the duodenum of a mammal, comprising:
    a spine having a proximal end and a distal end;
    a first atraumatic feature positioned adjacent to the spine proximal end;
    a second atraumatic feature positioned adjacent to the spine distal end, wherein a length of the spine is selected so that when the first atraumatic feature is in a stomach the second atraumatic feature is in the duodenum; and
    a plurality of flow reduction elements positioned along the spine, each flow reduction element having a proximal portion with a first porosity and a distal portion with a second porosity, the first porosity greater than the second porosity such that the proximal portion permits a flow of chyme into an interior portion of the flow reduction element while the distal portion at least partially inhibits the flow of chyme out of the interior portion of the flow reduction element.

14. The device of claim 13 wherein each flow reduction element is formed from a material selected to adjust the flow characteristics of chyme or ingesta relative to the material.

15. The device of claim 13 wherein the distal portion of each flow reduction element is a solid to retain the chyme within the interior portion.

16. The device of claim 13 wherein the plurality of flow reduction elements are configured to deform in shape in response to the peristaltic action of the duodenum.

17. The device of claim 13 wherein the length of the spine is selected so that when the first atraumatic feature is positioned in the stomach, the second atraumatic feature is positioned within the duodenum in proximity to the ligament of Treitz.

18. The device of claim 13 wherein at least a portion of an interior or an exterior of each flow reduction element is at least partially coated with a lipid-philic material.

19. The device of claim 13 further comprising:
    a lipid-philic structure within each of the flow reduction elements.

20. The device of claim 19 wherein the lipid-philic structure within each flow reduction element is attached to the spine.

21. The device of claim 19 wherein the lipid-philic structure within each flow reduction element is attached to the flow reduction element.

* * * * *

UNITED STATES PATENT AND TRADEMARK OFFICE
CERTIFICATE OF CORRECTION

PATENT NO. : 9,072,861 B2
APPLICATION NO. : 13/769097
DATED : July 7, 2015
INVENTOR(S) : McKinley et al.

Page 1 of 1

It is certified that error appears in the above-identified patent and that said Letters Patent is hereby corrected as shown below:

In the Claims:

Claim 15, column 8, line 52; after "reduction element is" and before "solid to retain", delete "a".

Signed and Sealed this
Eighth Day of December, 2015

Michelle K. Lee
*Director of the United States Patent and Trademark Office*